(12) United States Patent
Ferrari et al.

(10) Patent No.: US 8,614,354 B2
(45) Date of Patent: Dec. 24, 2013

(54) PROCESS FOR THE SYNTHESIS OF CINACALCET HYDROCHLORIDE

(75) Inventors: Massimo Ferrari, Cenate Sotto (IT); Marcello Ghezzi, Cumo (IT); Matteo Bonaldi, Schilpario (IT)

(73) Assignee: Erregierre S.p.A., San Paolo d'Argon (IT)

( * ) Notice: Subject to any disclaimer, the term of this patent is extended or adjusted under 35 U.S.C. 154(b) by 81 days.

(21) Appl. No.: 12/999,648

(22) PCT Filed: Jun. 18, 2008

(86) PCT No.: PCT/IT2008/000404
§ 371 (c)(1),
(2), (4) Date: Dec. 17, 2010

(87) PCT Pub. No.: WO2009/153814
PCT Pub. Date: Dec. 23, 2009

(65) Prior Publication Data
US 2011/0105799 A1    May 5, 2011

(51) Int. Cl.
*C07C 211/00* (2006.01)
*C07C 209/00* (2006.01)

(52) U.S. Cl.
USPC ............................ 564/387; 564/336; 564/395

(58) Field of Classification Search
None
See application file for complete search history.

(56) References Cited

U.S. PATENT DOCUMENTS

| 4,748,184 A * | 5/1988 | Stout et al. ................ 514/422 |
| 6,211,244 B1 * | 4/2001 | Van Wagenen et al. ...... 514/649 |
| 2007/0043243 A1 * | 2/2007 | Lifshitz-Liron et al. ...... 564/336 |
| 2007/0060645 A1 * | 3/2007 | Lifshitz-Liron et al. ...... 514/487 |

FOREIGN PATENT DOCUMENTS

| WO | 2007/127445 A2 | 11/2007 |
| WO | 2008/068625 A2 | 6/2008 |

OTHER PUBLICATIONS

Abdel-Magid, et al. J. Org. Chem. 1996, 61, 3849-3862.*
Pavia et al. "Introduction to Organic Laboratory Techniques", 1990, pp. 577-578.*

* cited by examiner

*Primary Examiner* — Clinton Brooks
(74) *Attorney, Agent, or Firm* — Gifford, Krass, Sprinkle, Anderson & Citkowski, P.C.

(57) ABSTRACT

There is described a process for the preparation of cinacalcet hydrochloride (I) which includes the steps of: a) reacting (R)-(+)-1-(1-naphthyl)ethylamine (II) with 3-[3-(trifluoromethyl)phenyl]propenaldehyde (III) to afford the non isolated intermediate (R)—N-[3-[3-(trifluoromethyl)phenyl]-2-propenylimino-N-[1-(1-naphthyl)ethylamine (IV); b) reducing the non isolated intermediate (R)—N-[3-[3-(trifluoromethyl)phenyl]-2-propenylimino-N-[-1-(1-naphthyl)ethylamine (IV) with a sequential addition of:—a solution of sodium borohydride, methanol and a base,—oxalic acid and—a base to obtain (R)—N-[3-[3-(tifluoromethyl)phenyl]-2-propenyl]-1-(1-naphthyl)ethylamine (V) by passing through the precipitation of the oxalate salt of compound (V) after the addition of oxalic acid; c) hydrogenating (R)—N-[3-[3-(trifluoromethyl)phenyl]-2-propenyl]-1-(1-naphthyl)ethylamine (V) thus obtaining (R)—N-(3-(3-(trifluoromethyl)phenyl]propyl]-1-(1-naphthyl)ethylamine cinacalcet base (VI), which is retaken in ethyl acetate; and d) treating the solution of cinacalcet base (VI) in ethyl acetate with hydrochloric acid to afford cinacalcet hydrochloride (I).

9 Claims, No Drawings

PROCESS FOR THE SYNTHESIS OF CINACALCET HYDROCHLORIDE

CROSS-REFERENCE TO RELATED APPLICATIONS

This application is the U.S. national phase of PCT/IT2008/000404 filed Jun. 18, 2008.

FIELD OF THE INVENTION

The present invention relates to a process for the synthesis of cinacalcet hydrochloride.

STATE OF THE ART (R)—N-(3-(3-(trifluoromethyl)phenyl]propyl]-1-(1-naphthyl)ethylamine, which is also known by the name of Cinacalcet and may be identified as (R)-α-methyl-N-[3-[3-(trifluoromethyl)phenyl]propyl]-1-naphthalenemethan amine (I) according to CAS to nomenclature (CAS number 226256-56-0), consists of a free base of the corresponding hydrochloride salt having the following structure and CAS number CAS 364782-34-3:

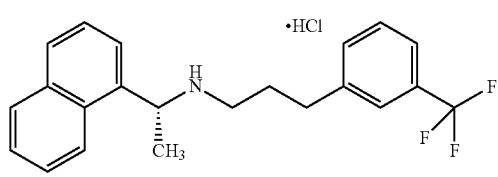 [SMILES: C[C@@H](NCCCc1cccc(C(F)(F)F)c1)c1cccc2ccccc12 ; Cl]

The cinacalcet molecule is an active ingredient employed in the treatment of hyperparathyroidism. It is a member of a family of calcimimetic compounds which may decrease the secretion of the parathyroid hormone (PHT) by activating calcium receptors.

The preparation of Cinacalcet has been disclosed for the first time in U.S. Pat. No. 6,211,244. According to this document, the compound indicated by number 22J is prepared by reacting 1-acethylnaphthalene with 3-[3-(trifluoromethyl)phenyl]propylamine in the presence of titanium isopropoxide to produce the corresponding cinacalcet isoimine, which is then converted to Cinacalcet through the treatment with sodium cyanoborohydride in methanol and the following chiral resolution through chiral liquid chromatography of the racemic mixture obtained. Alternatively, the same document U.S. Pat. No. 6,211,244 discloses a process for the preparation of cinacalcet, which includes the treatment of 3-fluoromethylcinnamonitrile with diisobutyl aluminum hydride, thus obtaining the aluminum-imine intermediate, which is treated with (R)-1-(1-naphthyl)ethylamine, and reducing the imine cinacalcet intermediate thus formed with sodium cyanoborohydride in ethanol.

In the paper Drug of the Future, 2002, 27(9), 831-836 a synthesis of cinacalcet is suggested which implies the reaction of (R)-(1-naphthyl)ethylamine with 3-[3-(trifluoromethyl)phenyl]propionaldehyde in the presence of tetraisopropoxy titanium to afford the corresponding cinacalcet imine, which is reduced to cinacalcet with NaBH$_3$CN in ethanol.

The above disclosed processes however require the use of reagents such as titanium isopropoxide, which is extremely toxic and flammable as well as not being environmentally sound. These reagents therefore make the industrial application of the process difficult.

U.S. Pat. No. 7,250,533 suggests a process that includes the step of converting 3-[3-(trifluoromethyl)phenyl]propylalcohol so as to substitute the hydroxyl group with a leaving group and combine the product thus obtained with (R)-1-naphthyl-ethylamine, in the presence of a base, at a temperature in the range from 50° C. to 120° C. for a time sufficient to obtain cinacalcet. Specifically, the step of converting 3-[3-(trifluoromethyl)phenyl]propylalcohol requires the combination of 3-[3-(trifluoromethyl)phenyl]propylalcohol in an aprotic organic solvent with a compound having a good leaving group, maintaining this reaction mixture at a temperature from about 0° C. to about 50° C. Although this process does not use disadvantageous reactive agents, it is however difficult to be scaled industrially.

Therefore, it is the object of the present invention to provide a process for the preparation of cinacalcet and the hydrochloride salt thereof, which is simple and easily industrially applicable while still displaying a good yield of final product.

SUMMARY

The object set forth above has been achieved by means of a process for the preparation of cinacalcet hydrochloride (I)

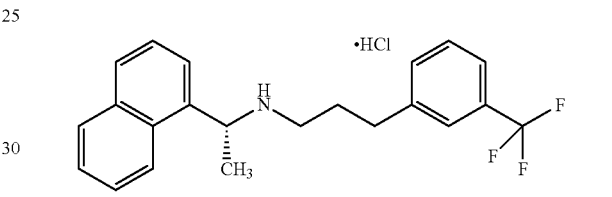

which includes the following steps:

a) reacting (R)-(+)-1-(1-naphthyl)ethylamine (II) with 3-[3-(trifluoromethyl)phenyl]propenaldehyde (III) to afford the non isolated intermediate (R)—N-[3-[3-(trifluoromethyl)phenyl]-2-propenylimino-N-[1-(1-naphthyl)ethylamine (IV)

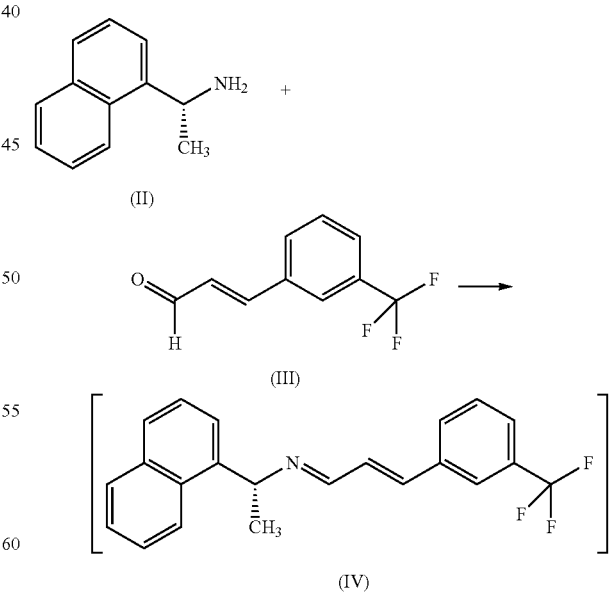

b) reducing the non isolated intermediate (R)—N-[3-[3-(trifluoromethyl)phenyl]-2-propenylimino-N-[1-(1-naphthyl)ethylamine (IV) with a sequential addition of:
  sodium borohydride, methanol and a base, oxalic acid,
a base,
to obtain (R)—N-[3-[3-(trifluoromethyl)phenyl]-2-propenyl]-1-(1-naphthyl)ethylamine (V) by passing through the precipitation of the oxalate salt of compound (V) after the addition of oxalic acid;

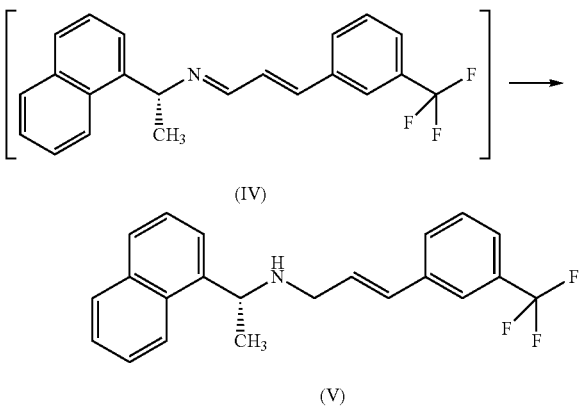

c) hydrogenating (R)—N-[3-[3-(trifluoromethyl)phenyl]-2-propenyl]-1-(1-naphthyl)ethylamine (V) thus obtaining (R)—N-(3-(3-(trifluoromethyl)phenyl]propyl]-1-(1-naphthyl)ethylamine cinacalcet base (VI), which is retaken in ethyl acetate;

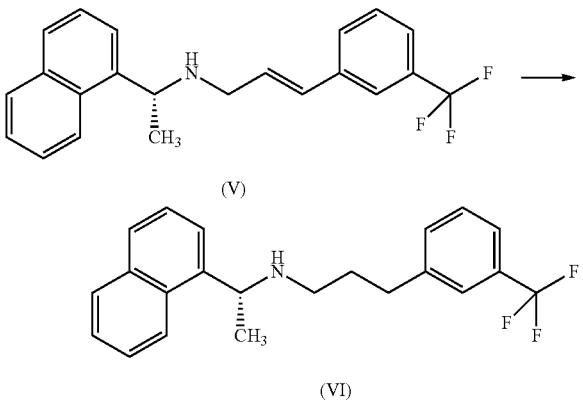

d) treating the solution of cinacalcet base (VI) in ethyl acetate with hydrochloric acid to afford cinacalcet hydrochloride (I).

DETAILED DESCRIPTION

The invention therefore relates to a process for the preparation of cinacalcet hydrochloride (I) which includes the steps of: a) reacting (R)-(+)-1-(1-naphthyl)ethylamine (II) with 3-[3-(trifluoromethyl)phenyl]propenaldehyde (III) to afford the non isolated intermediate (R)—N-[3-[3-(trifluoromethyl)phenyl]-2-propenylimino-N-[1-(1-naphthyl)ethylamine (IV); b) reducing the non isolated intermediate (R)—N-[3-[3-(trifluoromethyl)phenyl]-2-propenylimino-N-[1-(1-naphthyl)ethylamine (IV) with a sequential addition of:—a solution of sodium borohydride, methanol and a base,—oxalic acid and—a base to obtain (R)—N-[3-[3-(trifluoromethyl)phenyl]-2-propenyl]-1-(1-naphthyl)ethylamine (V) by passing through the precipitation of the oxalate salt of compound (V) after the addition of oxalic acid; c) hydrogenating (R)—N-[3-[3-(trifluoromethyl)phenyl]-2-propenyl]-1-(1-naphthyl)ethylamine (V) thus obtaining (R)—N-(3-(3-(trifluoromethyl)phenyl]propyl]-1-(1-naphthyl)ethylamine cinacalcet base (VI), which is retaken in ethyl acetate; and d) treating the solution of cinacalcet base (VI) in ethyl acetate with hydrochloric acid to afford cinacalcet hydrochloride (I). Preferably, the step a) of reacting (R)-(+)-1-(1-naphthyl)ethylamine (II) with 3-[3-(trifluoromethyl)phenyl]propenaldehyde (III) to afford the non isolated intermediate (R)—N-[3-[3-(trifluoromethyl)phenyl]-2-propenylimino-N-[1-(1-naphthyl)ethylamine (IV) occurs in the presence of methanol.

More preferably, the step a) of reacting (R)-(+)-1-(1-naphthyl)ethylamine (II) with 3-[3-(trifluoromethyl)phenyl]propenaldehyde (III) in the presence of methanol to afford the non isolated intermediate (R)—N-[3-[3-(trifluoromethyl)phenyl]-2-propenylimino-N-[1-(1-naphthyl) ethylamine (IV) occurs by stirring the reaction mixture at a temperature of about 20-30° C. The intermediate (R)—N-[3-[3-(trifluoromethyl)phenyl]-2-propenylimino-N-[1-(1-naphthyl)ethylamine (IV) is not isolated but instead is formed in the reactor and is immediately converted to (R)—N-[3-[3-(trifluoromethyl)phenyl]-2-propenyl]-1-(1-naphthyl)ethylamine (V) in step is b).

In step b) of the process of the invention, sodium borohydride, methanol and a base, oxalic acid and a base are sequentially added. The base is preferably a solution of an alkali metal hydroxide, more preferably a solution of sodium hydroxide, even more preferably a 30% sodium hydroxide solution. After the addition of oxalic acid, the solution is preferably heated to about 80° C. and then cooled to 0-30° C., thus achieving the precipitation of the oxalate salt of compound (V), which is then dissolved with the base.

In step c) (R)—N-[3-[3-(trifluoromethyl)phenyl]-2-propenyl]-1-(1-naphthyl)ethylamine (V) is subjected to a hydrogenation step. This hydrogenation occurs preferably by means of hydrogen on a palladium catalyst, more preferably hydrogen at a pressure of 0.2-1.5 atm. After washing and filtering the catalyst, the compound (R)—N-(3-(3-(trifluoromethyl)phenyl]propyl]-1-(1-naphthyl)ethylamine (VI) is retaken in ethyl acetate.

In step d) the solution of (R)—N-(3-(3-(trifluoromethyl)phenyl]propyl]-1-(1-naphthyl)ethylamine (VI) in ethyl acetate is treated with hydrochloric acid, preferably as hydrochloric acid gas, more preferably at a temperature of 30-50° C.

The process according to the invention therefore allows to achieve cinacalcet through a simple process which may easily be scaled industrially and employs reagents which are easier to handle and dispose of as compared to processes according to the prior art.

The invention will now be described with reference to some examples of the process according to the invention by way of non limitative illustration.

Example 1

Preparation of (R)—N-[3-[3-(trifluoromethyl)phenyl]-2-propenyl]-1-(1-naphthyl)ethylamine (V): Steps a) and b) of the Process According to the Invention 23.1 Kg of (R)-(+)-1-(1-naphthyl)ethylamine, 150.2 Kg of methyl alcohol, 27.7 Kg of 3-[3-(trifluoromethyl)phenyl]propenaldehyde were loaded in a reactor. The mass was stirred at a temperature of 20-30° C. for a few hours, thereby obtaining the non isolated intermediate (R)—N-[3-[3-(trifluoromethyl)phenyl]-2-propenylimino-N-[1-(1-naphthyl)ethylamine (IV)

in a methanol solution. The intermediate was reduced by pouring a solution of 3.9 Kg of sodium borohydride dissolved in 46.2 Kg of methanol and 0.6 of 30% sodium hydrate in the mass. The mass was stirred at a temperature of 0-20° C. until the Schiff base was reduced. 4.9 Kg of 80% acetic acid were then poured and methanol was distilled. 207.9 Kg of toluol and 138.6 Kg of water were added to the residue and the mass was stirred, separated and then the aqueous phase was discarded.

The toluene phase was titrated to determine the content of (R)—N-[3-[3-(trifluoromethyl)phenyl]-2-propenyl]-1-(1-naphthyl)ethylamine (V).

About 44.8 Kg of 100% product were achieved, equivalent to a yield of 93.5%. The toluene solution was then distilled to an oily residue, which was retaken with 176.8 Kg of N,N-dimethylformammide. 8.2 Kg of oxalic acid were added to the solution thus obtained.

The mass was heated to about 80° C. and once the solution was obtained, the solution was cooled to 0-30° C. until the oxalate salt precipitated. The oxalate salt was then filtered and washed with 22.4 Kg of N,N-dimethylformammide. 42.3 Kg of oxalate salt of the intermediate (R)—N-[3-[3-(trifluoromethyl)phenyl]-2-propenyl]-1-(1-naphthyl)ethylamine (V) were obtained, equivalent to a yield of 83.8%. 42.3 Kg of the oxalate salt of the intermediate (R)—N-[3-[3-(trifluoromethyl)phenyl]-1]-2-propenyl]-1-(1-naphthyl)ethylamine (V) were mixed with 210 Kg of toluol, 100 Kg of water and 8.5 Kg of 30% sodium hydroxide. The mass was stirred at a temperature of 20-70° C. when it was completely dissolved and the aqueous phase was separated and discarded.

The toluene solution obtained and containing the intermediate (R)—N-[3-[3-(trifluoromethyl)phenyl]-2-propenyl]-1-(1-naphthyl)ethylamine (V) was used in the hydrogenating step c) of Example 2.

Example 2

Preparation of (R)—N-[3-[3-(trifluoromethyl)phenyl]-2-propenyl]-1-(1-naphthyl)ethylamine Cinacalcet Base (VI)

The toluene solution containing the intermediate (R)—N-[3-[3-(trifluoromethyl)phenyl]-2-propenyl]-1-(1-naphthyl)ethylamine (V) resulting from 42.3 Kg of the oxalate salt of the intermediate (R)—N-[3-[3-(trifluoromethyl)phenyl]-2-propenyl]-1-(1-naphthyl)ethylamine (V) of Example 1 and 2.5 Kg of 5% Pd/C were loaded in a hydrogenator.

The solution was then hydrogenated at a temperature of 10-30° C. and at a pressure of 0.2-1.5 atm of hydrogen, until the complete saturation of the double bond occurred. The catalyst was discarded by filtration.

The organic phase was washed with 12 Kg of 80% acetic acid and 40 Kg of water (to eliminate the possible traces of (R)-(+)-1-(1-naphthyl)ethylamine). The organic phase was distilled to an oily residue, which was then retaken with 180 Kg of ethyl acetate.

The ethyl acetate phase was titrated to determine the content of "cinacalcet base".

About 30.0 Kg of 100% (R)—N-[3-[3-(trifluoromethyl)phenyl]propyl]-1-(1-naphthyl)ethylamine (VI) were obtained, equivalent to a yield of 79.4%.

Example 3

Preparation of Cinacalcet Hydrochloride

The entire ethyl acetate phase containing 30.0 Kg of 100% cinacalcet base was loaded in a reactor.

3.1 Kg of hydrochloric acid gas were bubbled at a temperature of 30-50° C. and the mass was stirred at a temperature of 30-50° C. until the product precipitated. The mass was thus cooled to 0-30° C. and filtered washing with 30 Kg of ethyl acetate. The product was dried, thus obtaining 30 Kg of Cinacalcet hydrochloride.

Yield: 90.6%

The invention claimed is:
1. A process for the preparation of cinacalcet hydrochloride (I)

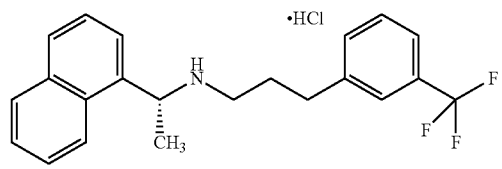

which includes the following steps:
a) reacting (R)-(+)-1-(1-naphthyl)ethylamine (II) with 3-[3-(trifluoromethyl)phenyl]propenaldehyde (III) to afford the non isolated intermediate (R)—N-[3-[3-(trifluoromethyl)phenyl]-2-propenylimino-N-[1-(1-naphthyl)ethylamine (IV)

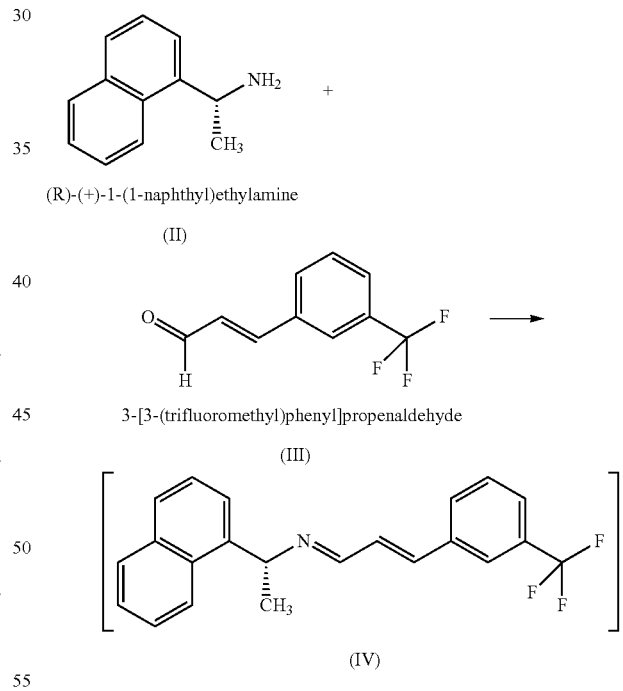

b) reducing the non isolated intermediate (R)—N-[3-[3-(trifluoromethyl)phenyl]-2-propenylimino-N-[1-(1-naphthyl)ethylamine (IV) with a sequential addition of:
sodium borohydride, methanol and a base,
oxalic acid, and
a base,
to obtain (R)—N-[3-[3-(trifluoromethyl)phenyl]-2-propenyl]-1-(1-naphthyl)ethylamine (V) by passing through the precipitation of the oxalate salt of compound (V) after the addition of oxalic acid;

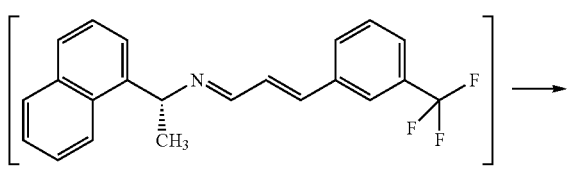

(IV)

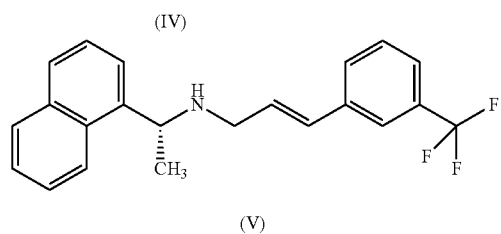

(V)

c) hydrogenating (R)—N-[3-[3-(trifluoromethyl)phenyl]-2-propenyl]-1-(1-naphthyl)ethylamine (V) thus obtaining (R)—N-(3-(3-(trifluoromethyl)phenyl]propyl]-1-(1-naphthyl)ethylamine cinacalcet base (VI), which is retaken in ethyl acetate;

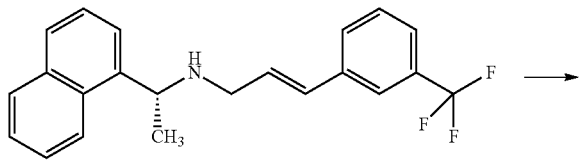

(V)

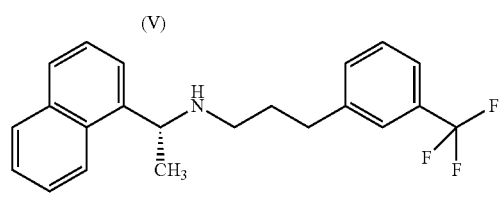

(VI)

d) treating the solution of cinacalcet base (VI) in ethyl acetate with hydrochloric acid to afford cinacalcet hydrochloride (I).

2. The process according to claim 1, wherein step a) of reacting (R)-(+)-1-(1-naphthyl)ethylamine (II) with 3-[3-(trifluoromethyl)phenyl]propenaldehyde (III) occurs in the presence of methanol.

3. The process according to claim 1, wherein step a) of reacting (R)-(+)-1-(1-naphthyl)ethylamine (II) with 3-[3-(trifluoromethyl)phenyl]propenaldehyde (III) occurs by stirring the reaction mixture at a temperature of 20-30° C.

4. The process according to claim 1, wherein in step b) the base is an alkali metal hydroxide solution.

5. The process according to claim 4, wherein the solution of alkali metal hydroxide is a solution of sodium hydroxide.

6. The process according claim 1, wherein in step b) after the addition of oxalic acid, the solution is heated to a temperature of about 80° C. and then cooled to a temperature of 0-30° C., thus obtaining the precipitation of the oxalate salt of compound (V).

7. The process according to claim 1, wherein in step c) (R)—N-[3-[3-(trifluoromethyl)phenyl]-2-propenyl]-1-(1-naphthyl)ethylamine (V) is hydrogenated by means of hydrogen on a palladium catalyst.

8. The process according to claim 7, wherein hydrogen is hydrogen at a pressure of 0.2-1.5 atm (atmospheres).

9. The process according to claim 1, wherein in step d) the solution of (R)—N-(3-(3-(trifluoromethyl)phenyl]propyl]-1-(1-naphthyl)ethylamine (VI) in ethyl acetate is treated with hydrochloric acid gas at a temperature of 30-50° C.

* * * * *